US008769754B2

(12) United States Patent
Byeon

(10) Patent No.: US 8,769,754 B2
(45) Date of Patent: Jul. 8, 2014

(54) ELECTRIC TOOTHBRUSH

(71) Applicant: LG Innotek Co., Ltd., Seoul (KR)

(72) Inventor: Daegil Byeon, Seoul (KR)

(73) Assignee: LG Innotek Co., Ltd., Seoul (KR)

( * ) Notice: Subject to any disclaimer, the term of this patent is extended or adjusted under 35 U.S.C. 154(b) by 0 days.

(21) Appl. No.: 13/953,246

(22) Filed: Jul. 29, 2013

(65) Prior Publication Data

US 2013/0305466 A1 Nov. 21, 2013

Related U.S. Application Data

(63) Continuation of application No. 13/082,884, filed on Apr. 8, 2011, now Pat. No. 8,499,396.

(30) Foreign Application Priority Data

Apr. 8, 2010 (KR) .................. 10-2010-0032374

(51) Int. Cl.
*A61C 17/34* (2006.01)

(52) U.S. Cl.
USPC ............................................. 15/22.1; 15/22.2

(58) Field of Classification Search
USPC ........... 15/22.1, 22.2, 23, 21.1, 22.3, 22.4, 28
See application file for complete search history.

(56) References Cited

U.S. PATENT DOCUMENTS

| | | | | |
|---|---|---|---|---|
| 3,060,474 A | * | 10/1962 | Woog | 15/22.1 |
| 4,235,253 A | * | 11/1980 | Moore | 132/322 |
| 8,156,599 B2 | * | 4/2012 | Waguespack et al. | 15/104.94 |
| 8,499,396 B2 | * | 8/2013 | Byeon | 15/22.1 |
| 2002/0120991 A1 | * | 9/2002 | Cacka et al. | 15/22.1 |
| 2004/0227418 A1 | * | 11/2004 | Kim | 310/81 |
| 2006/0156496 A1 | * | 7/2006 | Häfliger et al. | 15/22.1 |
| 2009/0091178 A1 | | 4/2009 | Waguespack et al. | |
| 2011/0289703 A1 | | 12/2011 | Häfliger et al. | |

FOREIGN PATENT DOCUMENTS

| | | |
|---|---|---|
| CN | 1762309 A | 4/2006 |
| CN | 201320225 Y | 10/2009 |
| JP | 2002-45379 A | 2/2002 |
| KR | 10-2007-0069446 A | 7/2007 |

OTHER PUBLICATIONS

Office Action dated Sep. 14, 2010 in Korean Application No. 10-2010-0032374, filed Apr. 8, 2010.
Office Action dated Mar. 13, 2013 in Chinese Application No. 201110087497.1, filed Apr. 8, 2011.

* cited by examiner

*Primary Examiner* — Shay Karls
(74) *Attorney, Agent, or Firm* — Saliwanchik, Lloyd & Eisenschenk

(57) ABSTRACT

Disclosed is an electric toothbrush including a toothbrush plate having a cleaning brush installed thereon; a toothbrush head having a storage within which the toothbrush plate is stored; a toothbrush body that is connected to the toothbrush head and has a storage space formed therein; a flat type vibration motor that is disposed between the toothbrush plate and the toothbrush head; and a power supply unit that includes a power supply that is disposed in the storage space of the toothbrush body and supplies the vibration motor with power, a power supply switch connected to the power supply and a wire that is electrically connected to the vibration motor and the power supply switch and supplies the vibration motor with power.

3 Claims, 2 Drawing Sheets

ELECTRIC TOOTHBRUSH

CROSS REFERENCE TO RELATED APPLICATIONS

This application is a continuation of U.S. Ser. No. 13/082,884, filed Apr. 8, 2011, which claims the benefit under 35 U.S.C. §119 of Korean Patent Application No. 10-2010-0032374, filed on Apr. 8, 2010, which are hereby incorporated by reference in their entirety.

BACKGROUND OF THE DISCLOSURE

1. Field of the Invention

The present disclosure relates to an electric toothbrush.

2. Description of Related Art

Generally, a toothbrush including a handle and a cleaning brush is formed with a plastic material. The toothbrush removes foreign substances and tartar (scale or dental calculus) from teeth by moving a user's wrist or arm.

Recently, an electric toothbrush is being increasingly used, which uses rotation and vibration of a motor in order to maximize effect of tooth brushing, i.e., to remove foreign substances or tartar from teeth using a toothbrush, and to make tooth brushing easy.

However, an electric toothbrush developed recently has a driving motor in its handle so that vibration generated by the driving motor embedded in the handle is not efficiently transferred to a cleaning brush. It is therefore difficult to efficiently remove the foreign substances and tartar from teeth.

BRIEF SUMMARY

The present disclosure provides an electric toothbrush, capable of directly vibrating a cleaning brush to obtain a high vibration on the cleaning brush, thereby efficiently removing foreign substances and tartar from teeth.

The technical problems to be solved by the present disclosure are not limited to the above technical problem, and other technical problems will be understood by those skilled in the art from the description below.

In an embodiment of the present disclosure, an electric toothbrush includes a toothbrush plate having a cleaning brush installed thereon; a toothbrush head having a storage within which the toothbrush plate is stored; a toothbrush body that is connected to the toothbrush head and has a storage space formed therein; a flat type vibration motor that is disposed between the toothbrush plate and the toothbrush head; and a power supply unit that includes a power supply that is disposed in the storage space of the toothbrush body and supplies the vibration motor with power, a power supply switch connected to the power supply and a wire that is electrically connected to the vibration motor and the power supply switch and supplies the vibration motor with power.

According to the electric toothbrush of the present disclosure, there is an advantageous effect that foreign substances and tartar can be removed from teeth by disposing a flat type vibration motor between a toothbrush plate having a cleaning brush installed thereon and a toothbrush head and by vibrating the cleaning brush directly from underneath the toothbrush plate.

DETAILED DESCRIPTION

Figure 1:
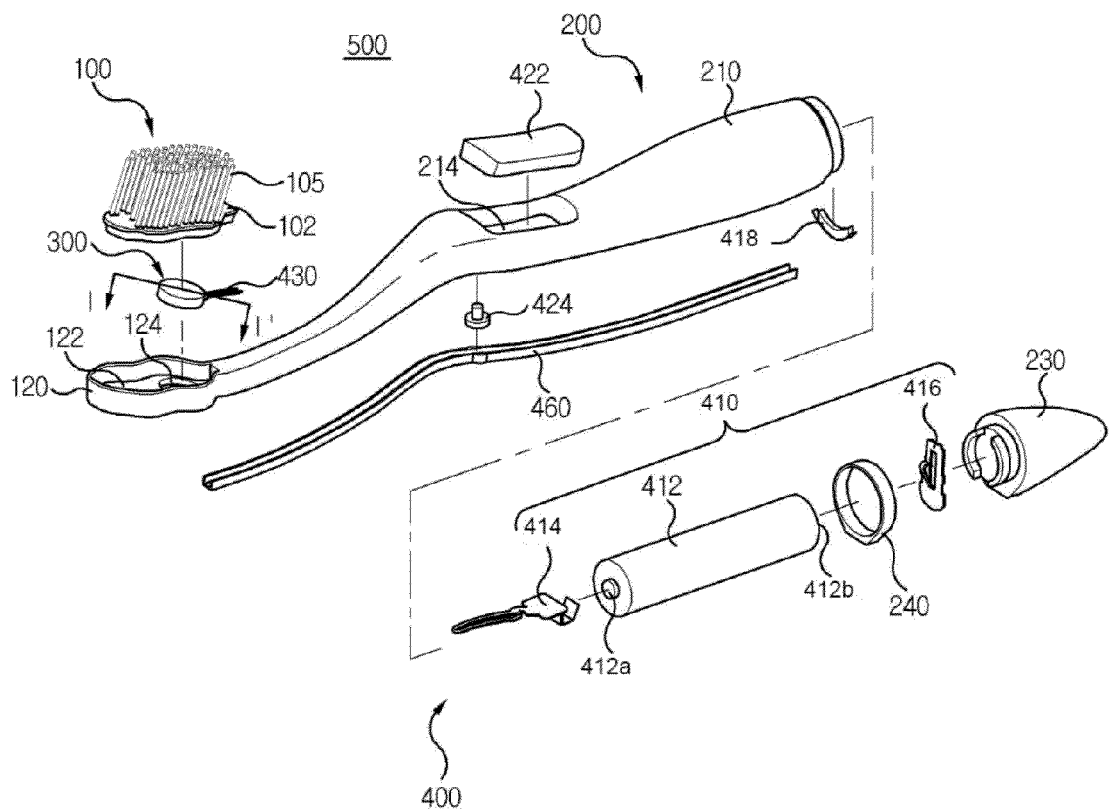
FIG. 1 is an exploded perspective view of an electric toothbrush according to an embodiment of the present disclosure.

Hereinafter, embodiments of the present disclosure will be described with reference to the accompanying drawings. In this procedure, size and shape of the components shown in the drawings may be exaggerated for the sake of clarity and convenience. Further, terms that are specifically defined in consideration of construction and operation of the present disclosure may be changed according to operator's intention or custom. Definition of such items should be made on the basis of entire contents of the specification.

Figure 2:
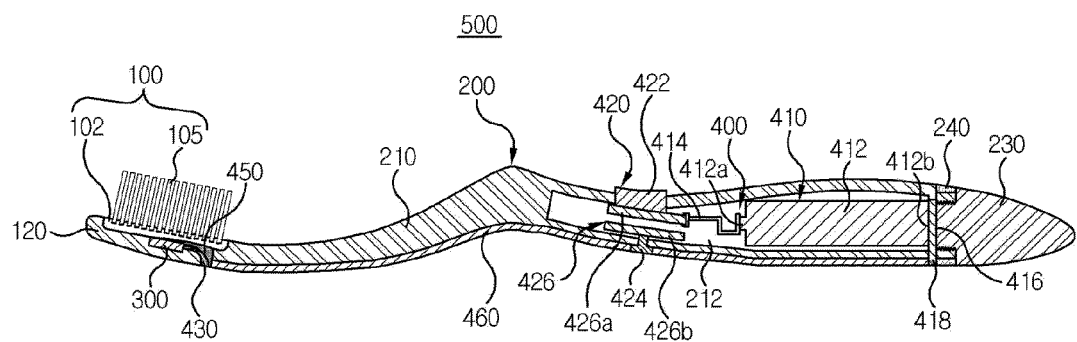
FIG. 2 is a sectional view of the electric toothbrush illustrated in FIG. 1.

FIG. 1 is an exploded perspective view of an electric toothbrush according to an embodiment of the present disclosure; FIG. 2 is a sectional view of the electric toothbrush illustrated in FIG. 1; and FIG. 3 is a view illustrating a bottom side of the electric toothbrush illustrated in FIG. 1.

Figure 3:
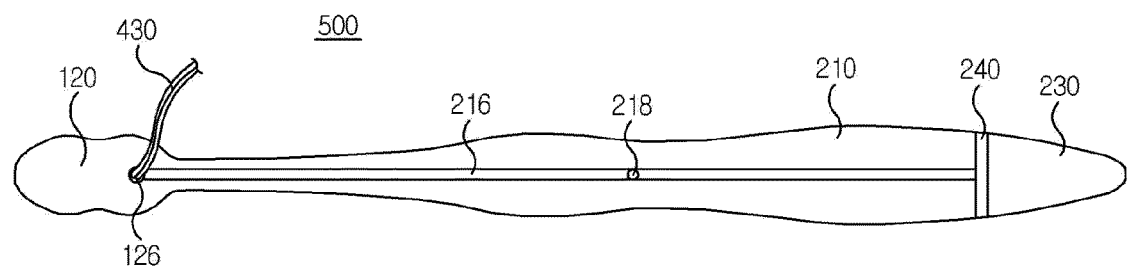
FIG. 3 is a view illustrating a bottom side of the electric toothbrush illustrated in FIG. 1.

Referring to FIGS. 1 to 3, the electric toothbrush 500 includes a toothbrush plate 100, a toothbrush head 120, a toothbrush body 200, a vibration motor 300, and a power supply unit 400. In addition, the electric toothbrush 500 includes a waterproof member 450 (refer to FIG. 2), and a sealing member 460.

The toothbrush plate 100 includes a base plate 102 to be described, that is formed correspondingly to the toothbrush head 120 and a cleaning brush 105 that is installed on the base plate 102 and removes foreign substances and tartar from teeth.

The toothbrush head 120 stores the toothbrush plate 100 and fixes it thereto. The toothbrush head 120 has a storage 122 being a concave groove to store the toothbrush plate 100, which is formed in the upper side of the toothbrush head 120, the upper side facing the base plate 102. A vibration motor storage groove 124 to be described that stores the vibration motor 300 is formed on the bottom of the storage 122.

The toothbrush head 120 has a wire discharge hole 126 formed as illustrated in FIG. 3.

The toothbrush plate 100 is fixed to the storage 122 of the toothbrush head 120 using an adhesive member or the like.

The toothbrush body 200 has a rod shape, which is integrally formed with the toothbrush head 120, and the toothbrush body 200 includes a first housing 210, a second housing 230 and a sealing holder 240.

The first housing 210 is defined as a portion gripped by a user's hand when a user brushes teeth, and one end of the first housing 210 is integrally formed with the toothbrush head 120.

A storage space 212 to be described that stores a power supply unit 400 is arranged in the first housing 210, which is formed from the middle of the first housing 210 to the end of the first housing 210 along longitudinal direction of the first housing 210.

A first button inserting hole 214 connected to the storage space 212 is formed on the top side of first housing 210 below which the storage space 212 is formed.

A wire storage groove 216 extending from a wire discharge hole 126 to the other end of the first housing 210 is formed on the bottom side of the first housing 210 that faces the top side of the first housing 210.

A second button inserting hole 218 is formed in a portion of the wire storage groove 216 corresponding to the first button inserting hole 214, which is also connected to the storage space 212.

The second housing 230 is thread-engaged with the other end of the first housing 210 so that it closes the storage space 212 of the first housing 210.

The sealing holder 240 is inserted between the first and second housings 210 and 230 so that it prevents water from being flown into the storage space 212 of the first housing 210.

Figure 4:
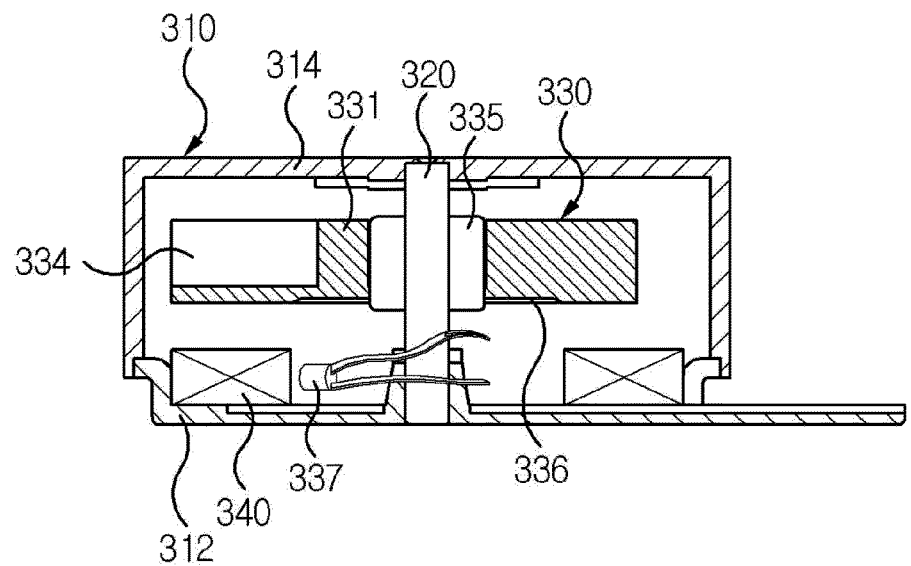
FIG. 4 is a sectional view of the vibration motor illustrated in FIG. 1, taken along line I-I'.

FIG. 4 is a sectional view of the vibration motor illustrated in FIG. 1, taken along line I-I'.

Referring to FIG. 4, the vibration motor 300 includes a flat type vibration motor, for example, and is disposed in a vibration motor storage groove 124 of the toothbrush head 120 to directly vibrate a cleaning brush 105 of the toothbrush plate 100. The vibration motor 300 includes a case 310, a rotational axis 320, a rotor 330 and a magnet 340.

The case 310 is formed in a coin shape, including a first case 312 and a second case 314 that is engaged with an upper portion of the first case 312. When the first and second cases 312 and 314 are engaged with each other, an empty space is formed in the first and second cases 312 and 314 to store the rotational axis 320, rotor 330 and magnet 340 therein.

The rotational axis 320 is vertically disposed in the case 310. One end of the rotational axis 320 is rotatably engaged with the center of the bottom surface of the first case 312, and the other end of the rotational axis 320 is rotatably engaged with the center of the upper side of the second case 314 that faces the bottom side of the first case 314.

The rotor 330 is fixed to the rotational axis 320 to be eccentric thereto, including a molding 331, a weight (not shown) and a pair of coils 334.

The molding 331 is formed in a disc shape and has a bearing 335 engaged in its center. Openings are formed around the bearing 335 to store the pair of coils 334 and a weight is disposed in the molding 331 to be eccentric thereto.

The weight is fixed to the rotational axis 320 to be eccentric thereto and generates a vibration when the rotational axis 320 rotates by a magnetic field that is generated by an interaction between the coil 334 and a magnet 340 to be described.

The coil 334 is wound around the weight 332 to generate a magnetic field needed to rotate the rotational axis 320.

The magnet 340 is formed in a doughnut shape and disposed on the bottom side of the first case 312 correspondingly to the coil 334. The magnet 340 rotates the rotational axis 320 by an inter-magnetic field interaction with the coil 334.

A reference numeral 336 in FIG. 4 denotes a commutator circuit board, and a reference numeral 337 denotes a brush, which is electrically connected to the commutator circuit board 336. In an embodiment of the present disclosure, the flat type vibration motor 300 may be formed in a brushless type.

In an embodiment of the present disclosure, construction and structure of the vibration motor 300 may be variously changed other than the vibration motor 300 illustrated in FIG. 4, and the embodiment of the present disclosure does not restrict the construction and structure of the vibration motor 300.

Referring to FIGS. 1 and 2 again, the power supply unit 400 is disposed in the storage space 212 of the toothbrush body 200 and supplies power to the vibration motor 300. The power supply unit 400 includes a power supply, a switch and a wire.

A power supply 410 includes a battery 412, an anode plate 414 and cathode plates 416 and 418.

The battery 412 supplies power needed to drive the vibration motor 300. An anode terminal 412a is formed on one side of the battery 412 and a cathode terminal 412b is formed on the other side of the battery 412. In an embodiment of the present disclosure, the battery 412 may be a nickel-cadmium battery, a nickel-hydrogen battery and a lithium ion battery.

The anode plate 414 is electrically in contact with the anode terminal 412a of the battery 412.

The cathode plates 416 and 418 include a first cathode plate 416 and a second cathode plate 418. The first cathode plate 416 is fixed to one end of the second housing 230 that is flown into the storage space 212 of the toothbrush body 200. Accordingly, when the second housing 230 is engaged with the first housing 210, the first cathode plate 416 is electrically in contact with the cathode terminal 412b of the battery 412.

The second cathode plate 418 is disposed in a thread engaging portion of the first housing 210. When the second housing 230 is thread-engaged with the first housing 210, the second cathode plate 418 is electrically in contact with the first cathode plate 416 fixed to the second housing 230.

The power supply switch 420 is disposed ahead of the power supply 410 in the storage space 212 of the toothbrush body 200, and forms a closed circuit together with the vibration motor 300, the power supply 410 and a wire to be described in order to supply power to the vibration motor 300.

The power supply switch 420 includes a first switch contact button 422, a second switch contact button 424 and a switch 426.

The first switch contact button 422 is inserted into a first button inserting hole 214 formed in the first housing 210 and the second switch contact button 424 is inserted into a second button inserting hole 218 formed in the first housing 210.

The switch 426 is disposed between the first and second switch contact buttons 422 and 424, and the switch 426 includes a first switch 426a and a second switch 426b.

The first switch 426a is a thin metal plate, which is disposed under the first switch contact button 422 and is electrically connected to the anode plate 414.

The second switch 426b is a thin metal plate, which is detached from the first switch 426a and is disposed on the second switch contact button 424.

When the first and second switch contact buttons 422 and 424 are pushed using user's thumb and forefinger, the first and second switches 426a and 426b are in contact with each other by a pressure applied to the first and second switch contact buttons 422 and 424 and then form an electrical closed circuit.

Referring to FIGS. 2 and 3 again, the wire 430 connects the vibration motor 300 and the power supply unit 400 with each other and supplies power needed to drive the vibration motor 300. The wire 430 includes an anode wire and a cathode wire.

The anode wire electrically connects the vibration motor 300 and the second spring with each other, and the cathode wire 434 electrically connects the vibration motor 300 and the second cathode plate 418 with each other.

The anode and cathode wires both connected to the vibration motor 300 are fetched out of the toothbrush head 120 through the toothbrush discharge hole 126 formed in the toothbrush head 120 and then stored in a wire storage groove 216 formed in the toothbrush body 200.

Referring to FIG. 2 again, a waterproof member 450 is formed to cover around the motor storage groove 124 including the vibration motor 300 in order to prevent water from flowing into the vibration motor 300 fixed to the vibration motor storage groove 126.

Referring to FIGS. 1 and 2 again, the sealing member 460 formed correspondingly to the wire storage groove 216 is inserted into the wire storage groove 216 including the wire discharge hole 126. The sealing member 460 prevents water from flowing into the vibration motor 300 through the wire discharge hole 126 and into the storage space 212 of the toothbrush body 200 through the wire storage groove 216.

According to the detailed description given above, the flat type vibration motor is installed between the toothbrush plate having the cleaning brush installed thereon and the toothbrush head so as to vibrate the cleaning brush directly from underneath the toothbrush plate, thereby sufficiently obtaining a vibration needed to remove foreign substances and tartar from teeth.

Hereinbefore, while the embodiments of the present disclosure are described, they are exemplary ones only and one of ordinary skill in the art may recognize that various alterations and modifications that fall within the scope of the present disclosure may be possible. Accordingly, the true technical protection scope of the present disclosure should be defined by the following claims.

What is claimed is:

1. An electric toothbrush, comprising:
    a toothbrush plate having a cleaning brush installed thereon;
    a toothbrush head having a storage within which the toothbrush plate is stored;
    a toothbrush body that is connected to the toothbrush head and has a storage space formed therein;
    a vibration motor that is disposed between the toothbrush plate and the toothbrush head;
    a power supply unit that includes a power supply that is disposed in the storage space of the toothbrush body and supplies the vibration motor with power, a power supply switch connected to the power supply and a wire that is electrically connected to the vibration motor and the power supply switch and supplies the vibration motor with power;
    an adhesive member to glue the toothbrush head and the toothbrush plate together; and
    a waterproof member to cover and protect the vibration motor;
    wherein the toothbrush head has a vibration motor storage groove to store the vibration motor, and
    wherein a wire storage groove to store a wire that is electrically connected to the vibration motor is formed on the surface of the toothbrush body, and the wire storage groove is engaged with a sealing member to seal the wire storage groove.

2. The electric toothbrush according to claim 1, wherein the vibration motor is formed in a flat coin shape.

3. The electric toothbrush according to claim 1, wherein the power supply switch includes:
    a first switch contact button disposed in the toothbrush body;
    a second switch contact button disposed in the toothbrush body and facing the first switch contact button; and
    a switch portion that is disposed in the storage space of the toothbrush body and is electrically connected by a pressure applied to the first and second switch buttons.

* * * * *